United States Patent [19]
Pennig

[11] Patent Number: 4,998,935
[45] Date of Patent: Mar. 12, 1991

[54] FOOT SUPPORTING EXTENSION FOR EXTERNAL FIXATION UNITS

[76] Inventor: Dietmar Pennig, Laukamp 11, D-4400 Münster, Fed. Rep. of Germany

[21] Appl. No.: 562,479

[22] Filed: Aug. 3, 1990

[30] Foreign Application Priority Data

Aug. 16, 1989 [DE] Fed. Rep. of Germany ....... 3926893

[51] Int. Cl.⁵ .......................... A61F 5/04; A61F 3/00
[52] U.S. Cl. ..................................... 606/54; 606/59; 128/80 R
[58] Field of Search .................... 606/53–60, 606/87, 80 R, 80 E, 80 J, 590, 593, 83.5, 882, 165, 166

[56] References Cited

U.S. PATENT DOCUMENTS

| | | | |
|---|---|---|---|
| 594,865 | 12/1897 | Fortney | 128/80 J |
| 1,863,188 | 6/1932 | Clash | 606/54 |
| 2,391,537 | 12/1945 | Anderson | 606/54 |
| 2,393,831 | 1/1946 | Stader | 606/56 |
| 2,406,987 | 9/1946 | Anderson | 606/56 |
| 3,086,522 | 4/1963 | Frohmader | 128/80 J |
| 4,135,505 | 1/1979 | Day | 606/54 |
| 4,312,336 | 1/1982 | Danieletto | 606/57 |
| 4,554,915 | 11/1985 | Brumfield | 606/54 |
| 4,621,627 | 11/1986 | Debastiani | 606/57 |
| 4,771,768 | 9/1988 | Crispin | 128/83.5 |
| 4,947,835 | 8/1990 | Hepburn | 606/56 |

OTHER PUBLICATIONS

"Manual de Osteosynthese", M. E. Müller et al. (Springer-Verlag, Berlin, Heidelberg New York, 1977), p. 311.

Primary Examiner—Robert A. Hafer
Assistant Examiner—Michael Brown
Attorney, Agent, or Firm—Peter K. Kontler

[57] ABSTRACT

A foot and ankle supporting and orienting extension for an external fixation unit with pins driven into the tibia of a patient has a coupling member which can be separably connected to a pin holder of a fixation unit, a variable-length carrier one end of which is articulately connected to the coupling member by a first universal joint and the other end of which is articulately connected to one end of a variabele-length link by a second universal joint, and a cushioned sole-contacting brace which is articulately connected to the other end of the link by a third universal spherical joint. By properly selecting the mutual inclination of the coupling member, carrier, link and brace relative to each other and/or by properly selecting the length of the carrier and/or the link, the patient or another authorized person can move the cushion of the brace to an optimum position relative to the sole of a foot forming part of a leg wherein the tibia is pinned to a fixation unit. This ensures that the foot and the ankle can rest in an optimum orientation. The joints can be locked to prevent articulation of the carrier, coupling member, link and brace relative to each other as soon as the cushion of the brace assumes an optimum position relative to the sole.

14 Claims, 1 Drawing Sheet

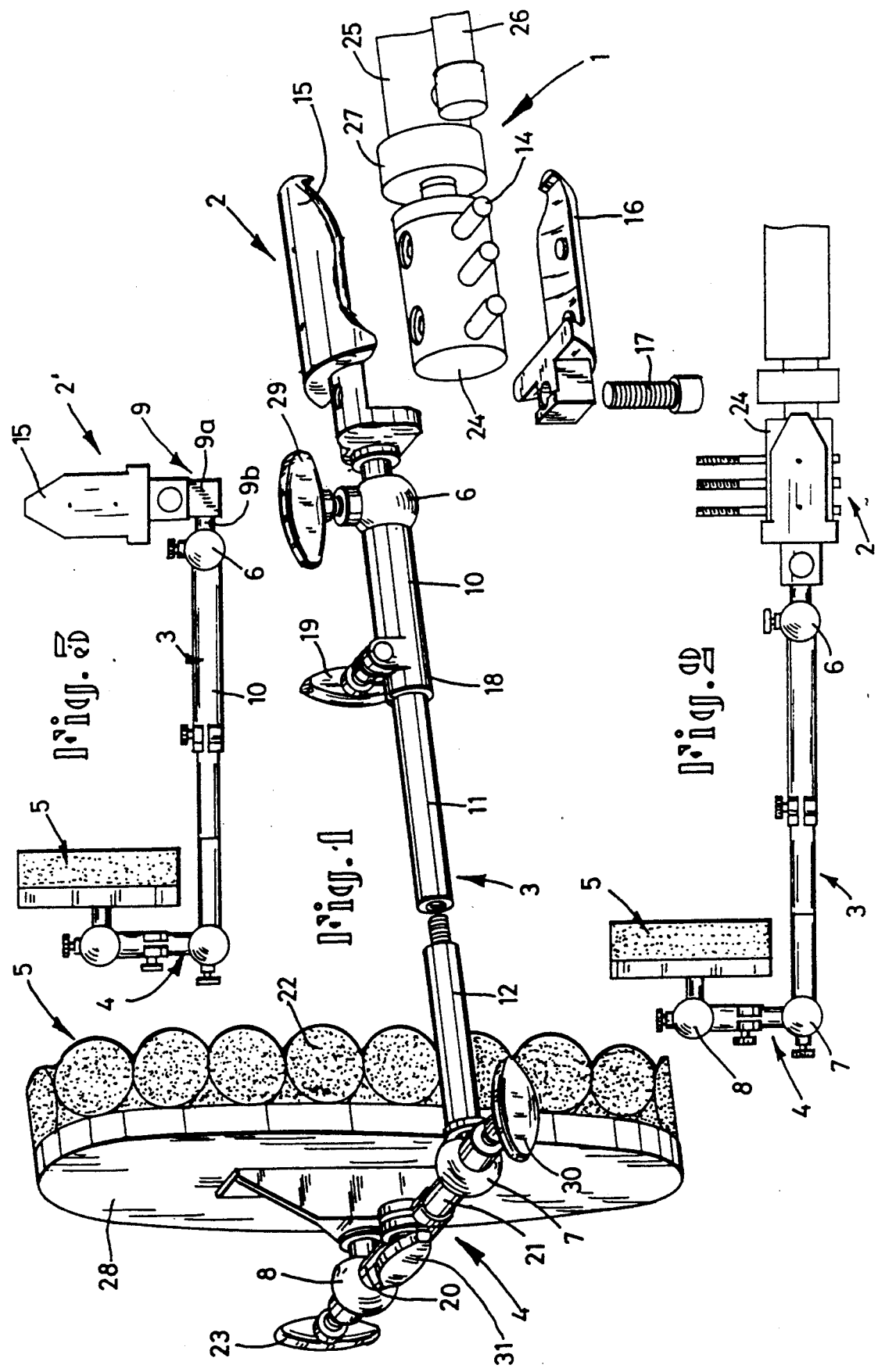

FOOT SUPPORTING EXTENSION FOR EXTERNAL FIXATION UNITS

BACKGROUND OF THE INVENTION

The invention relates to osteosynthetic instruments in general, and more particularly to improvements in so-called external fixation units which can be used to rigidly secure parts or fragments of a broken, cracked or diseased bone to each other for extended periods of time. Still more particularly, the invention relates to novel and improved means for enhancing the versatility and utility of external fixation units.

An external fixation unit which can be used to rigidly connect parts of broken bones is disclosed, for example, in U.S. Pat. No. 4,312,336 to Danieletto et al. The patented fixation unit comprises two spaced-apart clamping devices (hereinafter called holders) for pins which are to be driven into parts of a broken bone at opposite sides of the fracture, and a so-called central body member with a cylinder secured to one of the holders and a rod which is reciprocable in the cylinder and carries the other holder. The cylinder and rod can be fixed to each other to maintain the two holders at a desired distance from one another. In addition, the holders are articulately connected to the respective parts (cylinder and rod) of the central body member by universal joints which can be locked in selected positions. The parts of the patented fixation unit are made of a metallic material. Such so-called unilateral fixation units can be used with advantage to prevent movements of parts of a fractured bone (e.g., parts of tibia) relative to each other.

When a conventional fixation unit is applied to a tibia and the patient is resting on her or his back, the toes of the foot forming part of the injured leg extend upwardly. This renders it necessary to repeatedly or continuously exercise or massage the foot. Fixing of the foot in a desirable normal position by resorting to a rigid bandage is not always possible because such bandage would interfere with blood circulation. Moreover, the foot is likely to have been injured which is another reason why the physician or the nurse cannot resort to a bandage. Exercising or massaging of the foot is not possible if the patient has suffered brain damage, e.g., in the course of an accident which resulted in a fracture of the tibia.

Page 311 of the German-language publication "Manual der Osteosynthese" by M. E. Müeller et al. (Springer-Verlag Berlin Heidelberg New York 1977) shows that an external fixation unit for a fractured tibia can be equipped with a platform which is movable longitudinally of the tibia into or from abutment with the sole of the foot forming part of an injured leg. The fixation unit is a substantially triangular frame having three longitudinally extending frame members, namely two beneath the one at a level above the fractured tibia. The platform for the sole of the foot is movable longitudinally of the two lower frame members toward and away from as well as upwardly and downwardly and laterally of the frame members. Such movability of the platform does not suffice to ensure an optimum orientation of the platform relative to the foot and/or to ensure adequate support for the foot and the ankle of the injured leg.

OBJECTS OF THE INVENTION

An object of the invention is to provide a novel and improved extension which can be used in conjunction with available external fixation units for the tibia to support and orient the foot and the ankle of the injured leg in an optimum and comfortable position for the patient.

Another object of the invention is to provide an extension which can be used with a unilateral fixation unit and can be transferred from fixation unit to fixation unit with little loss in time.

A further object of the invention is to provide novel and improved means for enhancing the versatility and utility of existing external fixation units for fractured bones, especially for fractured shinbones.

An additional object of the invention is to provide an extension which can be applied and adjusted by a patient, a nurse, a physician or any other person with a minimum of effort, without resorting to any tools or by resorting to readily available rudimentary tools.

Still another object of the invention is to provide a simple but versatile extension which can be reliably secured to pin holders of unilateral external fixation units irrespective of the orientation of such holders relative to the broken bone.

SUMMARY OF THE INVENTION

The invention resides in the provision of a supporting and orienting device for the ankle and for the foot of a leg wherein the tibia carries an external osteosynthetic fixation unit (e.g., across a fracture of the tibia). The improved device can be said to constitute an extension of an external fixation unit and comprises a coupling member which is connectable to an external fixation unit (e.g., to a holder of pins which are driven into the tibia adjacent the ankle of the injured or diseased leg), an elongated variable-length carrier having a first end adjacent and a second end remote from the coupling member (the carrier serves to extend along the ankle of the leg wherein the tibia carries a fixation unit), a first joint having means for articulately connecting the first end of the carrier with the coupling member, a brace (e.g., in the form of a plate) which serves to abut the sole of the foot forming part of the leg wherein the tibia carries a fixation unit, a link between the brace and the second end of the carrier, a second joint having means for articulately connecting the second end of the carrier with the link, and a third joint having means for articulately connecting the link with the brace. The three joints, the variable-length carrier and the link enable a patient, a nurse, a physician or another person to properly orient the brace relative to the foot so that the sole of the foot can abut and can be supported by the brace and the latter indirectly supports and orients the ankle of the patient in an optimum position.

The coupling member preferably comprises means for separably attaching the first joint to an external fixation unit. Such attaching means can comprise a pair of shells which serve to receive a portion (e.g., the aforementioned holder of pins) of a fixation unit between them, and fastener means for clamping the shells against the holder of the fixation unit.

At least one of the joints can constitute a universal joint, e.g., a ball and socket joint. Furthermore, at least one of the joints preferably comprises means for releasably locking the respective connecting means (such as a ball and a socket) in a selected position.

The coupling member can comprise an adapter with mutually inclined first and second leg members. The aforementioned attaching means then serves to connect one leg member of the adapter to the fixation unit, and the first joint is interposed between the other leg member of the adapter and the first end of the carrier. The adapter can constitute a substantially L-shaped body wherein the two leg members make an angle of at least close to 90 degrees. Such adapter can be used with advantage if the pin holder of the fixation unit extends transversely of the tibia because the adapter cooperates with the first joint to permit positioning of the carrier in substantial parallelism with the tibia, along the ankle and to the second joint.

The link can include means for varying the distance between the second and third joints. Such variable-length link can include two or more sections which are slidably telescoped into each other and means for releasably locking the sections in selected positions, i.e., for releasably maintaining the second and third joints at a selected distance from each other. The link is or can be a straight link.

The carrier can include means for infinitely varying the distance between its first and second ends, i.e., between the first and second joints. For example, the carrier can include a first section which includes the first end, a second section which includes the second end and is movable toward and away from the first end between a plurality (e.g., an infinite number) of positions, and means for fixing the second section in a selected position with reference to the first section.

The brace can include a platform and a sole-contacting cushion of foam rubber or the like on the platform. The platform is articulately connected with the link by the third joint. The brace can have a substantially round or oval shape.

The novel features which are considered as characteristic of the invention are set forth in particular in the appended claims. The improved extension itself, however, both as to its construction and the mode of using the same, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a partly exploded perspective view of a foot supporting extension which embodies one form of the invention, a portion of an external fixation unit being shown between the shells of the coupling member.

FIG. 2 is a smaller-scale plan view of the assembled extension and with the coupling member in engagement with a pin-holding component of an external fixation unit; and FIG. 3 is a plan view of a modified extension wherein the coupling member includes a U-shaped adapter between the shells and the first joint.

DESCRIPTION OF PREFERRED EMBODIMENTS

FIG. 1 shows an end portion of an external axial fixation unit 1 which is or can be similar to that disclosed in the aforediscussed U.S. Pat. No. 4,312,336. The illustrated portion of the fixation unit 1 comprises a holder or clamping device 24 for a set of externally threaded pins 14 which are to be driven into a portion of a shinbone (not shown). FIG. 1 further shows a portion of a cylinder 25, a pressing or tensioning device 26, and an internally threaded ring 27 of the fixation unit.

The invention is embodied in a supporting and orienting device which can be used as a separable extension of the illustrated fixation unit 1 or another available fixation unit. The extensions of FIGS. 1 and 2 comprises a coupling member 2 with means (including two shells 15, 16 and a fastener 17) for separably attaching it to the pin holder 24 of the fixation unit 1, an elongated variable-length carrier 3 with a first end adjacent the coupling member 2, and a first joint 6 with means (such as a ball and a socket) for articulately connecting the first end of the carrier 3 to the coupling member 2. The extension further comprises a substantially plate-like brace 5 for the sole of the foot of a patient, a variable-length link 4, a second joint 7 with means for articulately connecting one end of the link 4 to the second end of the carrier 3, and a third joint 8 with means for articulately connecting the other end of the link 4 to a central portion of the rear side of a rigid platform or base 28 forming part of the brace 5. The latter further comprises a sole-contacting cushion or pad 22 which is glued or otherwise secured to the front side of the platform or base 23 and can be made of foam rubber or any other yieldable preferably elastic material.

When the shells 15, 16 of the coupling member 2 are properly assembled by means of the threaded fastener 17, they are clamped against the holder 24 in a manner as shown in FIG. 2, and the carrier 3 and link 4 can form a substantially L-shaped body which carries the brace 5 in such a way that the base 28 and the cushion 22 extend substantially at right angles to the carrier 3 and the patient can have the sole of the foot of her or his injured or diseased leg bear or merely abut the exposed side of the cushion 22 while the threaded portions of the pins 14 extend into the tibia of the leg. Of course, the joints 6, 7 and 8 render it possible to select any other suitable mutual inclination of the carrier 3 and shells 15, 16, of the carrier 3 and link 4 and/or of the link 4 and the plane of the base or platform 28 relative to each other. Each joint is or can constitute a spherical (ball and socket) joint of any conventional design, for example, of the type described and shown in the patent to Danieletto et al. FIG. 1 shows that the socket of the joint 6 carries a handle 29 with a threaded shank which can releasably lock the ball of the joint 6 in a selected position. A similar handle 30 is provided to lock the ball and socket of the joint 7 in a selected position. A third handle 23 performs a similar function in connection with the ball and socket of the joint 8 between the platform or base 28 and the link 4.

The length of the carrier 3 can be varied by removing a rod-like intermediate section 11 and by directly connecting a first section 10 (which carries one part of the joint 6 with a second section 12 (which carries one part of the joint 7). The section 10 is hollow and can receive a selected length of the section 11 or 12. The left-hand end portion 18 of the section 10 is slotted and the width of the slot can be varied by rotating a handle 19 which has a threaded shank mating with two lugs at opposite sides of the slot in the left-hand portion 18 of the section 10. If the carrier 3 is much too long, the section 11 is removed and the section 12 is inserted directly into the section 10. The sections 11 and 12 have mating male and female threaded portions.

The length of the preferably straight elongated link 4 can be varied in a manner similar to that of varying the length of the carrier 3. FIG. 1 shows that the link 4 comprises a hollow slotted section 20 which carries one part of the joint 8, a second section 21 which carries the other part of the joint 7 and extends into the section 20, and a rotary handle 31 having a threaded shank which mates with two lugs at opposite sides of the slot in the section 20. The overall length of the link 4 can be a small fraction of the length of the carrier 3.

The joint 6 enables the shell 15 of the coupling member 2 and the section 10 of the carrier 3 to move relative to each other about any one of a practically infinite number of different axes, and the same holds true for the movability of the link 4 and carrier 3 (joint 7) and link 4 and platform or base 28 (joint 8) relative to each other. All this enables the patient or another person to properly select the distance of the brace 5 from the fixation unit 1 as well as the inclination of the cushion 22 relative to the foot of the patient.

It will be appreciated that the coupling member 2 will be modified or replaced with a different coupling member if the design of the fixation unit is such that the illustrated coupling member 2 is not best suited to establish a separable connection between the joint 6 and the available fixation unit. Thus, if the fixation unit does not have a holder 24 of the type shown in FIGS. 1 and 2, the illustrated coupling member 2 will be replaced with a coupling member which can properly engage a differently configured component which is part of a fixation unit and is selected to separably support the improved extension.

FIG. 3 shows a modified extension which differs from the extension of FIGS. 1 and 2 in that the coupling member 2' comprises a substantially or exactly L-shaped adapter 9 having a first leg member 9a which is rigid with the shell 15 and a second leg member 9b which makes with the leg member 9a an angle of preferably 90 degrees and is rigid with one part of the joint 6. In all other respects, the extension of FIG. 3 is or can be identical with the extension of FIGS. 1 and 2. The adapter 9 is desirable and advantageous if the coupling member 2' must be applied transversely of the tibia. The adapter 9 then enables the carrier 3 to extend longitudinally of the tibia, the same as the carrier 3 of the extension which is shown in FIGS. 1 and 2. The section 10 of the adapter 3 of FIG. 3, the joint 6 and the coupling member 2' of FIG. 3 can be used interchangeably with the section 10, joint 6 and coupling member 2 of FIGS. 1 and 2.

The improved extension is susceptible of many additional modifications without departing from the spirit of the invention. For example, the means for releasably locking the balls and sockets of the illustrated spherical joints 6, 7 and 8 can be replaced with other locking means, the illustrated joints can be replaced with other types of joints, and the length of the carrier 3 and/or link 4 can be varied in any other suitable way. FIG. 1 shows that the illustrated brace 5 has a substantially circular or oval shape; if desired, the shape of the platform 28 and/or of the cushion 22 can more closely conform to the shape of a sole. Also, it is possible to furnish the extension with two or more braces having different sizes and/or shapes. The parts of the improved extension (other than the cushion 22) can be made of a suitable metallic material. However, it is equally possible to make at least some of the parts from a plastic material, e.g., in order to reduce the weight of the extension.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A supporting and orienting device for the ankle and the foot of a leg wherein the tibia carries an external osteosynthetic fixation unit, comprising a coupling member connectable to the fixation unit; an elongated variable-length carrier having a first end adjacent and a second end remote from said coupling member, said carrier being arranged to extend along the ankle of the leg wherein the tibia carries a fixation unit; a first joint having means for articulately connecting said first end with said coupling member; a brace arranged to abut the sole of the foot of a leg wherein the tibia carries a fixation unit; a link between said brace and said second end; a second joint having means for articulately connecting said second end with said link; and a third joint having means for articulately connecting said link with said brace.

2. The device of claim 1, wherein said coupling member comprises means for separably attaching said first joint to an external fixation unit.

3. The device of claim 1, wherein at least one of said joints is a universal joint.

4. The device of claim 1, wherein said at least one joint is a spherical joint.

5. The device of claim 1, wherein at least one of said joints further comprises means for releasably locking the respective connecting means in a selected position.

6. The device of claim 1 wherein said coupling member comprises an adapter having mutually inclined first and second leg members, and means for separably attaching one of said leg members to a fixation unit, said first joint being interposed between the other of said leg members and said first end.

7. The device of claim 6, wherein said adapter is substantially L-shaped.

8. The device of claim 1, wherein said link includes means for varying the distance between said second and third joints.

9. The device of claim 8, wherein said link is straight.

10. The device of claim 1, wherein said carrier includes means for infinitely varying the distance between said first and second ends.

11. The device of claim 10, wherein said carrier includes a first section including said first end, a second section including said second end and being movable toward and away from said first end between a plurality of positions, and means for fixing said second section in a selected one of said plurality of positions.

12. The device of claim 1, wherein said brace includes a platform and a sole-contacting cushion on said platform.

13. The device of claim 1, wherein said coupling member comprises a pair of shells arranged to receive a portion of a fixation unit between them, and fastener means for clamping said shells against such portion of the fixation unit.

14. The device of claim 1, wherein said brace is substantially round or oval.

* * * * *